United States Patent [19]

Marchenko et al.

[11] Patent Number: 4,528,979
[45] Date of Patent: Jul. 16, 1985

[54] CRYO-ULTRASONIC SURGICAL INSTRUMENT

[75] Inventors: Alexandr T. Marchenko; Eduard A. Bakai; Anatoly B. Rikberg; Valery L. Kutsevich; Alexandr N. Zhukov; Alexei I. Tsyganov; Alexandr V. Semenov; Alexandr I. Sugloba, all of Kiev; Valery N. Zaporozhan, Odessa; Jury V. Golubev Yanvarskogo, all of U.S.S.R.

[73] Assignees: Kievsky Nauchno-Issledovatelsky Institut Otolaringologii Imeni Professora A.S. Kolomiiobenka; Institut Fiziki Akademii Nauk Ukrainskoi SSR, both of U.S.S.R.

[21] Appl. No.: 359,250

[22] Filed: Mar. 18, 1982

[51] Int. Cl.³ ............................................. A61B 17/36
[52] U.S. Cl. ............................ 128/303 R; 128/303.1; 128/400
[58] Field of Search ..................... 128/303.1, 399, 400, 128/303 R, 24 A

[56] References Cited

U.S. PATENT DOCUMENTS

| 3,237,623 | 3/1966 | Gordon | 128/303.1 |
| 3,589,363 | 6/1971 | Banks et al. | 128/303 R |
| 3,911,924 | 10/1975 | Zimmer | 128/303.1 |
| 3,942,519 | 3/1976 | Shock | 128/303.1 X |

FOREIGN PATENT DOCUMENTS 989438  9/1951  France .............. 128/24 A

*Primary Examiner*—Lee S. Cohen
*Attorney, Agent, or Firm*—Burgess, Ryan & Wayne

[57] ABSTRACT

In a common housing are disposed an ultrasonic transmitter electrically coupled to a generator of electrical ultrasonic oscillations, and a cryodestructor communicating with a source of coolant medium. The working portion of the cryodestructor is disposed within the source of coolant medium.

13 Claims, 14 Drawing Figures

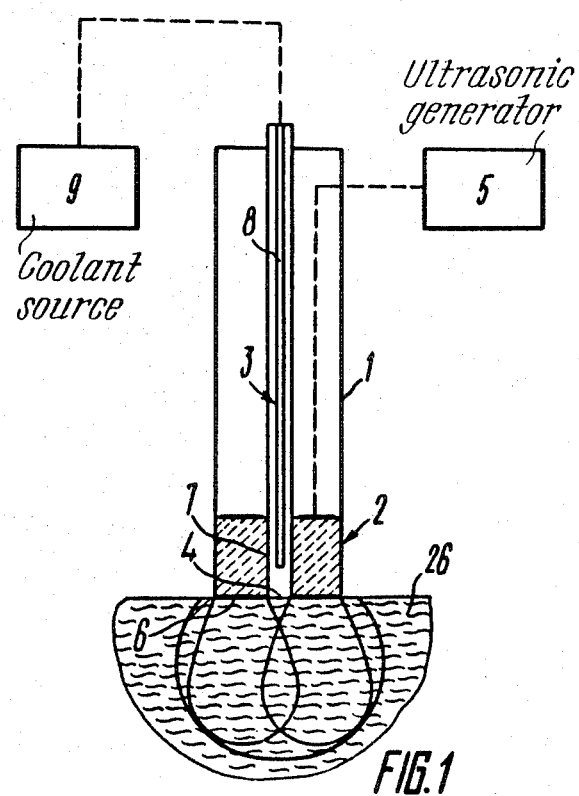
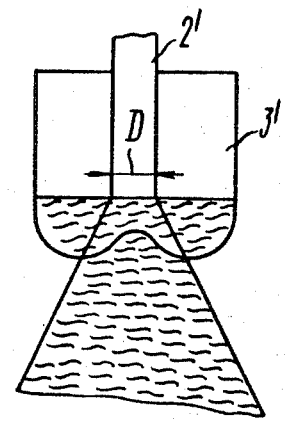
FIG. 2a  *Prior Art*
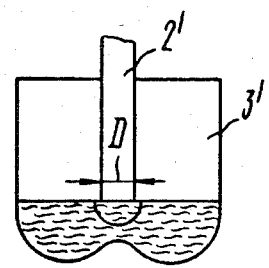
FIG. 2b  *Prior Art*

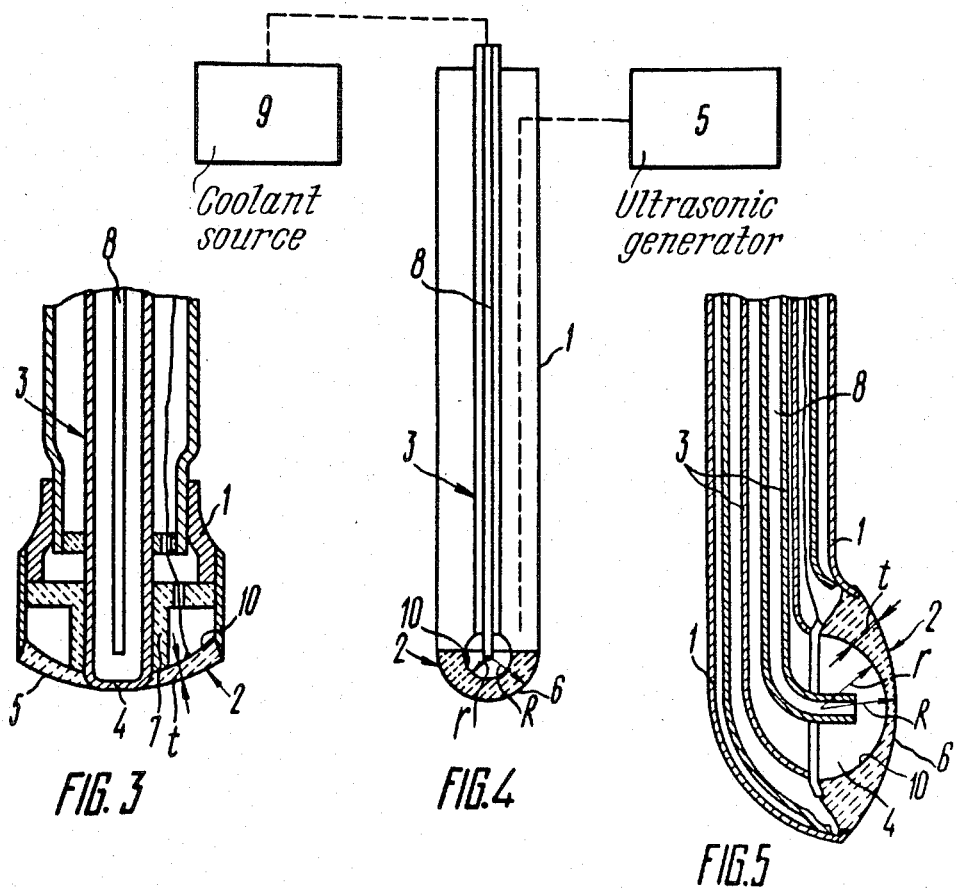

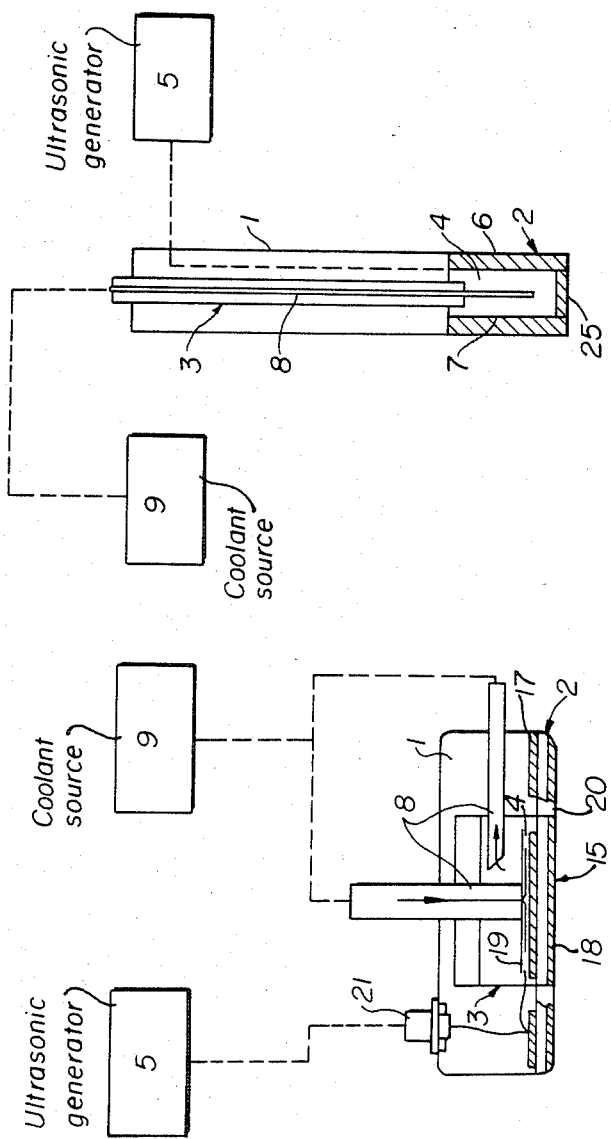

CRYO-ULTRASONIC SURGICAL INSTRUMENT

BACKGROUND OF THE INVENTION

1. Field of the Invention

The invention relates to medical equipment, and namely to devices for surgical treatment of pathologic structures of extended superficial regions of tissues, and particularly to cryo-ultasonic surgical instruments.

The invention can be used in clinical and ambulatory practice for surgical treatment of pathologic structures of local superficial regions of tissues, particularly malignant tumors and precancerous states. Instruments of this type may be utilized e.g. in dermatology and cosmetic medicine.

2. Prior Art

The inventive cryo-ultrasonic surgical instrument is designed for combined influence of deep freezing and ultrasound on a selected region of a tissue, thereby ensuring a relatively low traumatism of the procedure alongside with a high efficiency of treatment, simplicity of equipment and accessibility for surgeons of average skills.

It should be noted that prior art processes of cryogenic and therapeutic ultrasonic influences on tissues, which are used separately, are of significantly lower efficiency than the above mentioned combined influence.

Even in a rather deep freezing down to temperatures close to the boiling point of liquid nitrogen, viable cells may remain within the zone of influence, thereby creating the danger of recidivation, and in the cryogenic surgery of malignant tumors the danger of metastatic spreading.

To accomplish destruction of biological tissues by means of ultrasound, a high-power ultrasonic radiation above the stability threshold of cells and noncellular structures is generally used, which may adversely effect the organism as a whole.

In addition, in this case the complete destruction of the elements of pathologic structures is not guaranteed, and respectively relapses and metastases are not eliminated.

Moreover, to accomplish ultrasonic destruction under the specified conditions, unique ultrasonic generators and transmitters are required, which are inaccessible for ordinary clinics.

At present, surgical instruments are available, whose operation is based on a combination of cryogenic and ultrasonic influence on tissues. However, these instruments do not ensure high intensity of destruction of pathologic structures of these tissues due to the absence of geometric congruency between the zones of effective influence of each of the above factors.

Known in the art is a cryo-ultrasonic surgical instrument comprising a working portion performing ultrasonic oscillations. This portion is placed inside a device intended for cooling down to cryogenic temperatures (USSR Author's Certificate No. 460,869).

Destruction of a pathologic structure of a tissue is achieved in this instrument due to a mechanical tearing of the tissue under the effect of vibration of a working portion tip (saw) of the instrument at an ultrasonic frequency and a large amplitude. Due to the cooling, the tissues which are soft in the natural state, are frozen, which fact makes it possible to destruct them by the specified method. The forms of heat and acoustic fields, ensured by this instrument, are absolutely different, and the zone of their joint influence on a tissue is insignificant. Besides, the parameters of ultrasonic oscillations, required for the saw to accomplish mechanical destruction of the tissue, do not provide for a desired effect even within the zone where the above fields are congruent.

Another prior art cryo-ultrasonic surgical instrument comprises a cryodestructor disposed within a common housing and coupled to the source of a coolant medium, and an ultrasonic transmitter connected to a generator of electrical ultrasonic oscillations. The ultrasonic transmitter is disposed within a bore provided in the cryodestructor (U.S. Pat. No. 3,911,924).

Ultrasonic irradiation of tissues, accomplished by this instrument, however, has as its aim location of the freezing zone rather than destruction of said tissues, for which purpose an ultrasonic signal is formed as short impulses, and therefore it is impossible to ensure the intensity and time of ultrasonic irradiation required for combined influence on the tissue, because of a high pulse duty factor and a narrow directional pattern of an irradiation diagram also conditioned by location.

At the same time, in exciting continuous oscillations of the ultrasonic transmitter with required parameters, the above specified instrument cannot be practically utilized to carry out cryo-ultrasonic destruction since with the above described arrangement of the transmitter only a small portion of the total zone to be destructed is irradiated by an ultrasonic beam.

For this reason the destruction of a tissue occurs mainly under the effect of cryogenic temperatures, and the efficiency of combined influence of the above two factors on the tissue turns out to be low, which results in slowing down the reparation of tissues within the zone of necrosis and prolonging the term of treatment.

SUMMARY OF THE INVENTION

The object of the invention is the provision of an improved cryo-ultrasonic surgical instrument possessing an increased efficiency of influence on pathologic structure of tissues.

In particular, the object of the invention is the provision of a cryo-ultrasonic surgical instrument allowing the zones of effective influence of cryogenic temperatures and ultrasound to be combined within the zone being destructed.

Another object of the invention is the provision of a cryo-ultrasonic surgical instrument provided with a geometry of an ultrasonic transmitter, being rational for an organ being irradiated.

The next object of the invention consists in the provision of an economic cryo-ultrasonic surgical instrument.

A further object of the invention is to provide introducing the cryo-ultrasonic surgical instrument into the zone being destructed in the case of inner location thereof.

Another object of the invention is to increase the technological capabilities of a cryo-ultrasonic surgical instrument.

Still another object of the invention is to accelerate the reparation within the zone of necrosis and to reduce the terms of treatment.

The objects set forth and other objects of the invention are achieved by that in a cryo-ultrasonic surgical instrument comprising a generator of electrical ultrasonic oscillations, a cryodestructor provided with a working portion having ducts for communication with the source of a coolant medium, and an ultrasonic transmitter located within a common housing with the cryodestructor working portion and coupled to the generator of electrical oscillations, according to the invention, the working portion of the cryodestructor is disposed within the ultrasonic transmitter, the latter being an axiosymmetrical body.

The external dimensions of the transmitter in the claimed structure always correspond to the dimensions of the cryodestruction zone, the latter generally exceeding the size of the working portion of the cryodestructor by a magnitude of not more than 2 cm per side. Therefore, practically the whole zone being destructed is subjected to combined cryogenic and ultrasonic influence.

In this case, the effect of cryo-ultrasonic influence on pathologic structures of tissues is increased, which is expressed in the first place in an increase in the destruction extent to a value completely eliminating the presence of normal cellular elements within the zone of cryo-ultrasonic necrosis (the prior art cryo-ultrasonic instruments do not ensure such a destruction extent), and secondly in acceleration of tissue reparation within the zone of necrosis, which is further accompanied by a decrease in the terms of treatment.

Complete destruction of cells within the irradiation zone is promoted by emanation of lysosomic and proteolytic enzymes from the cells being destructed, said enzymes in turn destroying those cells which have survived after the combined effect.

An indirect evidence showing an increase in the efficiency of influence on a tissue as a result of the combination of deep freezing and ultrasonic irradiation lies in the fact that at an early stage following the cryo-ultrasonic effect, in a zone subjected to this effect, a greater number of macrophages infiltrating the tissue appears than at a corresponding stage following the cryogenic effect, which fact is known to be an indicator of high rate and quality of subsequent regeneration.

For the majority of cases in the surgical practice it is expedient that the ultrasonic transmitter be in the form of a solid of revolution. In this case the working portion of the cryodestructor can be disposed within the central bore of the transmitter.

For some cases, e.g. for the application of the instrument in dermatology, it is expedient that the ultrasonic transmitter be provided with a flat end face serving as a surface of acoustic contact. In this case the inner surface of the transmitter, which is opposite to said surface of acoustic contact, can be flat as well. Such an arrangement of the instrument of the invention makes it possible, for a destructor whose diameter is on the order of an ultrasonic wavelength in the tissue, to ensure cryodestruction of a superficial region of the tissue being of up to 40 mm in diameter on ultrasonically treating the whole zone being destructed.

In the cases where from the medical viewpoint it is necessary to reduce the outer diameter of the transmitter and to ensure cryo-ultrasonic destruction within a zone being beyond the limits defined by the area of direct acoustic contact, the surface of the ultrasonic transmitter which is opposite to the end surface of acoustic contact is constructed curvilinear and the ultrasonic transmitter has a thickness increasing from the axis of the instrument towards the periphery thereof, which arrangement can be ensured both by flat and curvilinear shapes of the end surface of acoustic contact.

For some operations, particularly gynecologic operations on ectocervix, the ultrasonic transmitter is expedient to be constructed of a shape being as close as possible to the geometry of the organ, for which purpose the end surface of acoustic contact of the ultrasonic transmitter should be made curvilinear.

Maximum expansion of directional pattern of an ultrasonic beam, and respectively the smallest diameter of the transmitter for the predetermined dimensions of a zone being irradiated can be obtained in the case where the surface of acoustic contact of the ultrasonic transmitter, facing with its convex outwardly, and the inner surface being opposite to the former surface, are constructed spherical with the radii R and r respectively, determined in accordance with the following expressions:

$$R = D/(2 \sin \phi_o);$$

$$r = R[1 - \cos \phi_o + \sin \phi_o \cdot \operatorname{ctg}(\phi_o + 45°)] - t_o,$$

$$\phi_o = 90° - \alpha - \arcsin 0.56 (V_o/V), \text{ and}$$

$$\alpha = \arcsin 0.52 (\lambda/D),$$

where
- D is the diameter of the surface of acoustic contact of the ultrasonic transmitter;
- $t_o$ is the minimum thickness of the transmitter between the surface of acoustic contact and the inner surface opposite thereto;
- $\lambda$ is the length of an ultrasonic wave within the medium being irradiated;
- $V_o$ is the speed of propagation of an ultrasonic wave within the medium being irradiated;
- V is the speed of propagation of an ultrasonic wave within the transmitter.

To achieve a uniform ultrasonic irradiation of the total zone being destructed, and especially in the cases where the dimensions of said zone exceed those of the ultrasonic transmitter, it is expedient that the generator of electrical ultrasonic oscullations be constructed as serially connected generator of sinusoidal oscillations, and frequency and amplitude modulators controlled by a master oscillator.

Periodic change of frequency and amplitude of ultrasonic oscillations carried out due to such an arrangement results in the fact that in the process of operation of the instrument different regions of the ultrasonic transmitter resonate. The configuration of directional pattern and intensity of irradiation of various regions of the zone being destructed vary correspondingly, an average intensity of irradiation being maintained constant.

To accomplish destruction of especially extended regions of tissues, the instrument can be provided with an additional ultrasonic transmitter, mounted on the end face of the working portion of the cryodestructor and being thermally insulated from the main ultrasonic transmitter.

To carry out destruction of the tissues disposed within tubular organs or narrow cavities whereto it is impossible to introduce the whole working portion of the instrument, it is expedient to dispose the cryodestructor within the central bore of the ultrasonic transmitter for axial displacement, thereby providing for the possibility of introducing only the working portion of the cryodestructor into the cavity, and to utilize the frozen tissue as a waveguide for the ultrasound.

To accomplish cryo-ultrasonic surgical cavitary operations, e.g. on larynx, esophagus, or in urologic operations, it is expedient to construct the ultrasonic transmitter in the form of a cylinder having a side surface of acoustic contact. The central bore of the transmitter in this case is also expedient to be made cylindrical. In the case where the length of the transmitter is to be reduced, the surface of acoustic contact and the opposing inner surface of the transmitter can be made barrel-shaped. Such a shape of the transmitter also facilitates introducing the instrument into the cavity. For the predetermined length of the region to be irradiated, the length of the transmitter will be the smallest provided that the thickness of its side wall increases in the longitudinal direction from the middle portion towards the end faces of the transmitter. It is also expedient that the above surfaces be spherical.

To accomplish cavitary operations accompanied by destruction of tissues disposed along the axis of the instrument, it is expedient to provide a blind central bore of the transmitter, so that at least a bottom portion of the wall of this bore can simultaneously serve as a working portion of the cryodestructor.

Also possible is such a modification of the instrument, wherein the whole external surface of the transmitter is a surface of acoustic contact, consisting from smoothly conjugated side surface of revolution and spherical end surface. Such an arrangement allows the uniformity of the ultrasonic field to be upgraded and the possibilities of the instrument to be expanded.

BRIEF DESCRIPTION OF DRAWINGS

The invention is further explained in terms of specific embodiments thereof with reference to the accompanying drawings, in which:

FIG. 1 shows schematically a cryo-ultrasonic surgical instrument of the invention, general view;

FIG. 2 (a, b) shows schematically a working portion of a prior art cryo-ultrasonic surgical instrument;

FIG. 3 shows a sectional view of a working portion of a cryo-ultrasonic surgical instrument according to the embodiment thereof provided with an end surface of acoustic contact;

FIG. 4 shows schematically an embodiment of the cryo-ultrasonic instrument of the invention, provided with a spherical end surface of acoustic contact and a spherical opposite inner surface of an ultrasonic transmitter;

FIG. 5 shows a sectional view of a modification of the cryo-ultrasonic surgical instrument of the invention illustrated in FIG. 4;

FIG. 8 shows schematically a modification of the cryo-ultrasonic surgical instrument of the invention provided with an additional ultrasonic transmitter;

FIG. 10 shows schematically a modification of the cryo-ultrasonic surgical instrument of the invention provided with a side surface of acoustic contact;

DETAILED DESCRIPTION OF THE INVENTION

Figure 7:
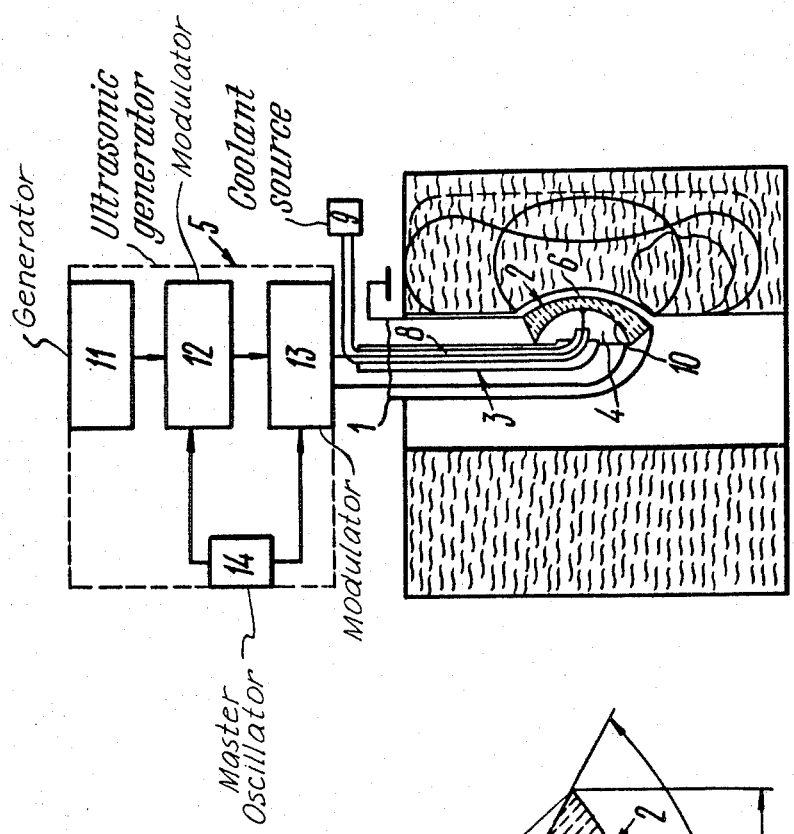
FIG. 7 shows schematically a modification of the cryo-ultrasonic surgical instrument of the invention, provided with a generator of electrical ultrasonic oscillations having periodically varied frequency and amplitude.

A cryo-ultrasonic surgical instrument comprises a housing 1 (FIG. 1) within which is mounted an ultrasonic transmitter 2 in the form of an axiosymmetrical body, and a cryo-destructor 3 whose working portion 4 is disposed within the transmitter 2.

In FIG. 2 (a,b), wherein for the purpose of comparison is shown the working portion of a prior art cryo-ultrasonic surgical instrument, an ultrasonic transmitter is designated by the numerical 2', and a cryodestructor in which is mounted the transmitter 2' is designated by the numerical 3'.

The ultrasonic transmitter 2 (FIG. 1) is electrically coupled to a generator 5 of electrical ultrasonic oscillations, and is a converter for transforming electrical oscillations into mechanical ones, constructed from a piezoceramic material. The most convenient form for the transmitter 2 is that of a solid of revolution, though it may be of some other shape which is mainly determined by the form of a region of a tissue to be irradiated.

A surface 6 of the transmitter 2, facing the tissue to be irradiated, is a surface of acoustic contact. In the simplest case it is a flat end face, providing for the possibility of utilizing the instrument for effecting superficial regions of the tissue.

The cryodestructor 3 is constructed as a rod and is inserted into a central bore 7 of the ultrasonic transmitter 2. In the cryodestructor 3 is provided a conduit 8 communicating with a source 9 of a coolant medium.

FIG. 3 illustrates a design drawing of the working portion of a cryo-ultrasonic surgical instrument of the invention wherein the surface 6 of acoustic contact of the transmitter 2, being an end face of the latter, is made curvilinear.

An inner surface 10 of the transmitter 2, being opposite to the above surface, is also made curvilinear, a thickness t of the transmitter 2 between said surfaces 6 and 10 being a variable value and increasing from the center towards the periphery of the solid of revolution, which is the ultrasonic transmitter 2. Due to such an arrangement there is ensured cryo-ultrasonic destruction of regions which are disposed both directly under the transmitter 2 and beyond the limits of the zone defined by the surface 6.

FIG. 4 illustrates an embodiment of the cryo-ultrasonic instrument of the invention wherein both surfaces 6 and 10 are made spherical. The surface 10 can be regarded in this case as a surface of either the whole wall or the bottom portion of the wall of the central bore, which is made blind. This bottom portion of the wall simultaneously serves as the working portion of the cryodestructor 3 since it defines a cavity filled with a coolant medium through the conduit 8.

The instrument of such an arrangement is mainly applicable for carrying out cavitary operations accompanied by destruction of tissues located along the axis of the instrument. The centers of spheres having a radius r for the surface 10, and a radius R for the surface 6 of acoustic contact may be displaced with respect to one another so that the thickness t of the transmitter will be variable and increasing from the center to the periphery, thereby providing for the same effect as in the instrument shown in FIG. 3.

FIG. 5 demonstrates a working portion of the instrument of the invention, applied mainly for treating superficial regions of tissues, which are hard-to access, e.g. within the cavities of larynx, esophagus etc.

On the inner spherical surface 10 of the transmitter 2 is disposed an inner electrode designed for connection to the generator 5.

An external electrode is disposed on the surface 6 of acoustic contact, which is also made spherical. The thickness t of the transmitter 2 increases from the center towards the periphery thereof.

Figure 6:
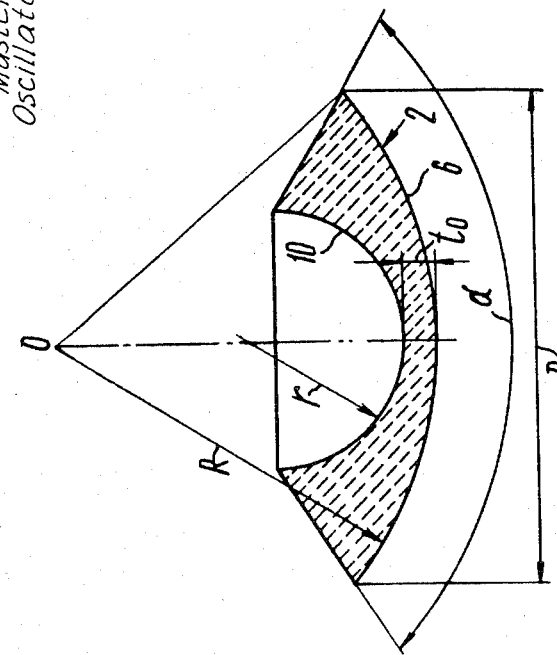
FIG. 6 shows an enlarged view of the ultrasonic transmitter of the cryo-ultrasonic surgical instrument illustrated in FIG. 5.

For the purpose of maximum expansion of directional pattern of ultrasonic irradiation, the radii r and R of the spheres of said surfaces 10 and 6 (FIG. 6) are selected from the following formulas:

$$R = D/(2 \sin \phi_o) \quad (1),$$

$$r = R[1 - \cos \phi_o + \sin \phi_o \cdot \text{ctg}(\phi_o + 45°)] - t_o \quad (2),$$

where
D is the diameter of the transmitter 2,
$\phi$ is the angle of inclination of the peripheral region of the convex working surface relative to the axis of the transmitter 2,
$t_o$ is the smallest thickness of the transmitter 2,
The angle $\phi_o$ is in turn determined depending on transmitter dimensions and properties of the material from which it is constructed, said angle being of $$\phi_o = 90° - \alpha - \arcsin 0.56 (V_o/V), \quad (3),$$

where
$\alpha$ is the angular width of the directional pattern,
$V_o$ is the speed of the ultrasonic wave propagation within the medium being irradiated,
V is the speed of the ultrasonic wave propagation within the ultrasonic transmitter 2.
The value of the angle $\alpha$ is determined as follows:

$$\alpha = \arcsin 0.52 (\lambda/D), \quad (4)$$

where $\lambda$ is the wavelength within the medium being irradiated.

The approximated value of $\alpha$ for all the parameters of the zone being irradiated is of 180°, which fact is caused by the combined effect of the surface 6 of acoustic contact, the peripheral region of the transmitter surface, inclined relative to the central axis thereof (the angle of inclination depends on the convexity of the surface 6), and the front of the ultrasonic wave within the transmitter 2 whose inclination depends on the nature of variation of the tramsmitter thickness between said surfaces 6 and 10.

In the case where the ratio between the radii r and R of the spheres, specified in the expressions 1 and 2, is not observed, the losses required for the transformation of electrical oscillations into mechanical ones become greater.

In the case where the surfaces 6 and 10 are constructed non-spherical, the efficiency of the transmitter is reduced due to the non-uniform nature of variations in the properties of the transmitter is reduced due to the non-uniform nature of variations in the properties of the transmitter along the diameter thereof. An incised form of the amplitude frequency characteristic and the directional pattern appears.

To accomplish uniform ultrasonic irradiation of the zone being destructed, and especially in the case of a broad directional pattern of the ultrasonic beam, which is ensured by the shape of the transmitter 2, the cryoultrasonic surgical instrument is provided with a generator of electrical ultrasonic oscillations whose amplitude and frequency are periodically varied, thereby allowing the intensity of the ultrasonic radiation to be equalized within the limits of the zone to be destructed. Such an instrument is illustrated in FIG. 7.

The generator 5 of electrical oscillations in this case comprises a generator 11 of sinusoidal oscillations, an ultrasonic frequency modulator 12, and an ultrasonic amplitude modulator 13, the above devices being connected in series and being any of conventional blocks of respective designations. The modulators 12 and 13 have their control inputs connected in parallel to a master oscillator 14, the latter being a triangular-pulse generator.

Another way of expanding the zone of cryo-ultrasonic effect, providing for the possibility of obtaining direct contact with the region of the tissue to be destructed, is realized by utilizing an additional ultrasonic transmitter 15 according to the modification of the cryo-ultrasonic instrument shown in FIG. 8.

Within the common housing 1 of this instrument are disposed the main ultrasonic transmitter 2 being a flat annular piezoelectric element provided with inner and outer electrodes 16 and 17, and the cryodestructor 3 disposed within the annulus bore, the additional ultrasonic transmitter 15 being fixed to the end face of the working portion 4 of said cryodestructor, the additional transmitter being a disc piezoelectric element provided with an outer and inner electrodes 18 and 19, and thermally insulated by a washer 20 from the main ultrasonic transmitter 2.

The cryodestructor 3 is in communication with the source 9 of a coolant medium by means of conduits 8. The electrodes 16 through 19 are connected by a plug connector 21 to the generator 5 of electrical ultrasonic oscillations.

Figure 9:
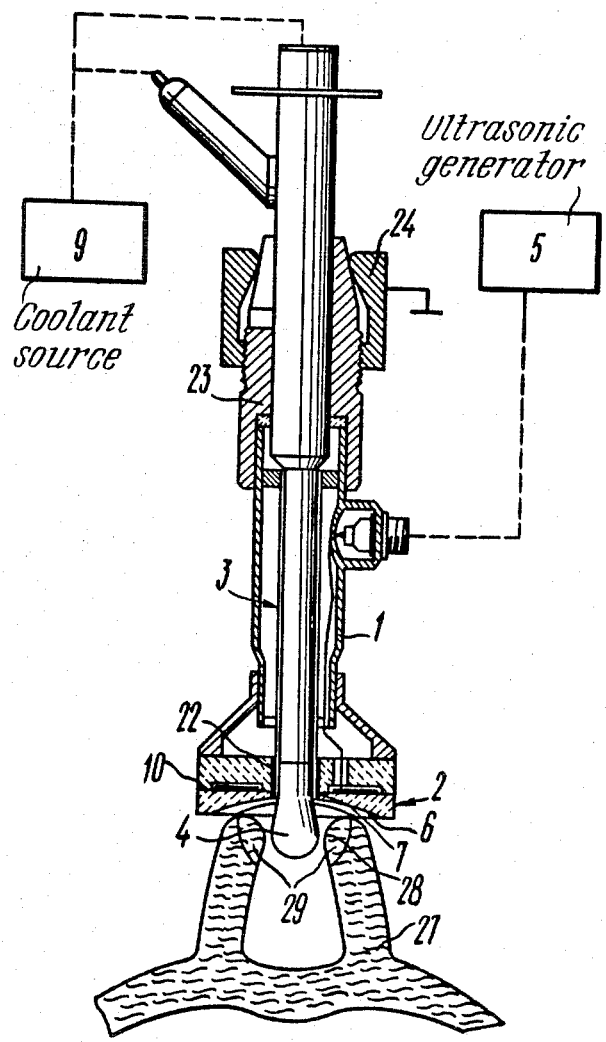
FIG. 9 shows schematically a modification of the cryo-ultrasonic surgical instrument of the invention provided with an axially movable cryodestructor.

In the embodiment demonstrated in FIG. 9 it is possible to accomplish diversity spacing the zones of thermal and acoustic contacts, which is sometimes required in irradiation of tissues being the walls of cavities whereto it is impossible to introduce the whole instrument.

In the ultrasonic transmitter 2 having a spherical concave end surface 6 of acoustic contact there is provided a through central bore 7, the working portion 4 of the cryodestructor passing therethrough. A ring 22 made from a heat-conducting material ensures a required thermal contact over the flat inner surface 10 between the cryodestructor 3 and transmitter 2. The cryodestructor 3 is mounted for axial displacement within the transmitter 2.

A collet 23 with a nut 24, fastened on the housing 1, is designed for fixing mutual location of the transmitter 2 and the cryodestructor 3, which location is determined by geometry of a cavity within which the region of the tissue to be irradiated is disposed.

When it is required to irradiate walls of a tubular organ, the surface 6 of acoustic contact can be provided in the form of a side surface of a solid of revolution, e.g. a cylinder. Such an embodiment of the invention is shown schematically in FIG. 10. A washer 25 insulates the tissues disposed along the axis of the instrument, from the cryogenic effect.

Figure 11:
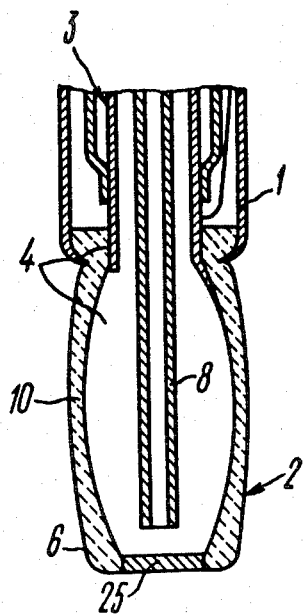
FIG. 11 shows the working portion of a modification of the cryo-ultrasonic surgical instrument illustrated in FIG. 10.

Curvilinear generating lines of the surface 6 of acoustic contact and of the inner surface 10 of the transmitter 2, as illustrated in FIG. 11, make it possible, while maintaining the same length of the destruction zone, to decrease the length of the transmitter 2 as against the length of a transmitter wherein both said surfaces are of cylindrical shape. The most advantageous from this viewpoint is a barrel-like shape of the transmitter 2 provided with spherical inner and outer surfaces and a wall of a variable thickness, increasing from the center towards the end faces. Here the same effect takes place as that mentioned in the variant of the end surface of acoustic contact, shown in FIG. 5. In addition, the instrument of such a configuration can be easier introduced into a tubular organ.

Figure 12:
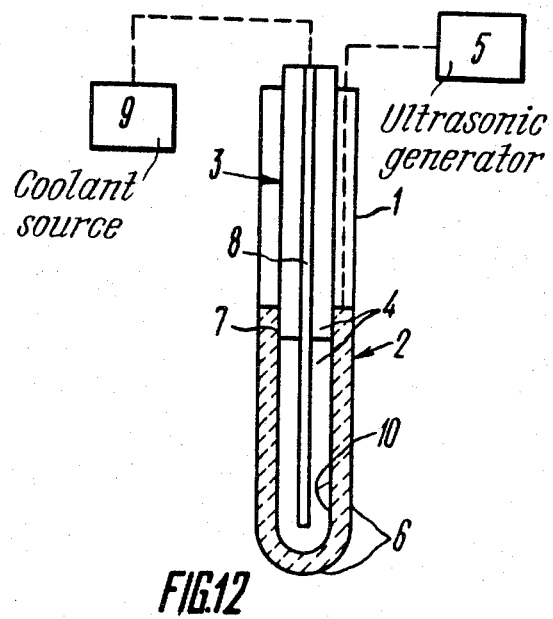
FIG. 12 shows schematically a modification of the cryo-ultrasonic instrument of the invention provided with a surface of acoustic contact encompassing side and end surfaces of the ultrasonic transmitter.

When it is desired to carry out all-round irradiation of walls of a cavity, the surface 6 of acoustic contact of the cryo-ultrasonic instrument may include both side and end surfaces of the transmitter 2, which surfaces in this case smoothly conjugate as shown in FIG. 12.

The cryo-ultrasonic surgical instrument operates as follows. The ultrasonic transmitter 2 (FIG. 1) and the cryodestructor 3 are brought into contact with the surface of a tissue 26 to be destructed, the thermal contact being achieved by pressing the cryodestructor 3 against the moistened tissue, while the acoustic contact additionally requires the presence of a contact medium stable to abrupt jumps in temperature, e.g. silicone oil. Then, cryodestruction of tissues is carried out by supplying a coolant medium, which is generally liquid nitrogen, from the source 9 into the working portion 4 of the cryodestructor 3. Simultaneously with the cooling or thereafter, the tissue 26 is subjected to the ultrasonic effect.

In FIGS. 1 and 2, dashed lines directed from below upwardly and from the left to the right designate the zone of the effective cryogenic influence, and the dashed lines directed from above downwardly and from the left to the right define the zone of the effective ultrasonic influence. The intersection of these dashed lines shows the zone of the effective combined cryo-ultrasonic influence.

It is seen from FIG. 1 that, when treating the tissue 26 by means of the cryo-ultrasonic instrument of the invention, the zones of effective cryogenic and ultrasonic effects coincide almost completely. They are not congruent only within a very small volume adjacent the end face of the cryodestructor 3, which is insignificant considering a small diameter of the latter.

The directional pattern of the ultrasonic beam of the prior art cryo-ultrasonic instrument, given for the purpose of comparison in FIG. 2, corresponds to the case of significant, e.g. tenfold, excess of the diameter D of the working portion of the ultrasonic transmitter 2 over the wavelength $\lambda$ of the ultrasonic radiation within a medium being irradiated (D=10 $\lambda$). For a still greater value of D, i.e. with D<10 $\lambda$, the divergence of the ultrasonic beam can be neglected, and the coincidence of zones of the effective influence of cryogenic temperatures and ultrasound will be worse than that illustrated in FIG. 2a.

In the case where the diameter D of the working portion of the transmitter 2 is less or equal to the wavelength $\lambda$ within a medium being irradiated, the transmitter 2 is essentially a point source of ultrasound, from which a spherical wave propagates (FIG. 2b). It is obvious that an intensity drop, j, along the wave front occurs in accordance with the law $j=j_o S_o/S$, where $j_o$ is a predetermined intensity of ultrasonic radiation, $S_o=2\pi r^2$, is the area of the hemisphere of the transmitter having a radius of r, $S=2\pi R^2$ is half the area of a sphere formed by the wave front.

It has been proved experimentally that for the maximum wavelength within the tissue, $\lambda=0.17$ cm, the intensity drop of radiation down to a value where said radiation does not provide a required effect occurs at a distance R=0.38 cm, which is practically equal to the absence of the cryo-ultrasonic effect.

In all other cases, i.e. for $\lambda<D<10$ $\lambda$, the directional pattern of the ultrasonic beam will correspond to an intermediate case and will not be congruent (within the specified limits of intensity) with the zone of cryodestruction.

Thus, when comparing the zones of effective cryogenic and ultrasonic influences of the claimed and prior art cryo-ultrasonic instruments on the tissue being destructed, it is obvious that the efficiency of combined influence of freezing and ultrasound in the case of utilization of the instrument of the invention is considerably higher as a result of maximum congruency between said zones.

It should be noted that in the embodiments of the cryo-ultrasonic instrument in accordance with FIGS. 4, 7, 8, and 12, the "dead" zone, in which the zones of cryogenic and ultrasonic influences are not congruent and which is characteristic of transmitters provided with a through central bore, is absent.

As shown in FIG. 7, for the embodiment of the cryo-ultrasonic surgical instrument illustrated therein, the zone of effective cryoultrasonic effect is considerably expanded and makes it possible to cover regions which are out of direct contact with the ultrasonic transmitter 2.

Figure 13:
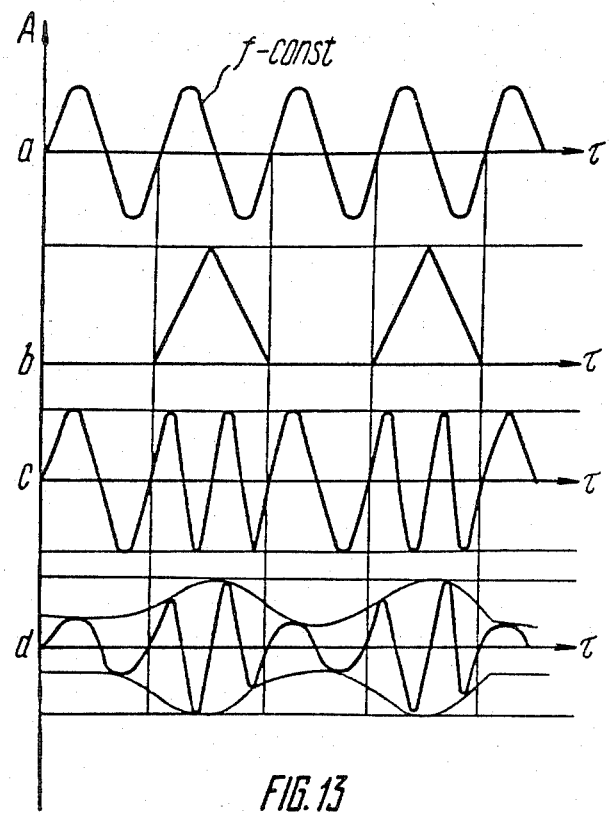
FIG. 13 (a through d) shows shape diagrams of output signals generated by the blocks incorporated into a generator of electrical ultrasonic oscillations.

An output signal of the generator 11 having a sinusoidal form (FIG. 13a) is supplied to the frequency modulator 12. Frequency modulation of the ultrasonic radiation is carried out by a triangular voltage which is formed by the master oscillator 14 (FIG. 13b) and is fed to the control input of the frequency modulator 12, which results in the appearance of a frequency-modulated signal at the output of said modulator (FIG. 13c), said signal being fed to the amplitude modulator 13.

Regulation of the amplitude is also carried out by a triangular voltage (FIG. 13b) being fed from the master oscillator 14 to the control input of the modulator 13 so that in increasing the frequency, the amplitude of oscillations also increases to compensate the frequency dependence of attenuation of ultrasound. Thus, at the output of the modulator 13 appears an amplitude and frequency-modulated signal (FIG. 13d), which is fed to the transmitter 2.

In accordance with the variations in the amplitude and frequency of the signal, the transmitter 2 at different moments resonates at each frequency with different regions thereof, thereby causing a change in the directional pattern from the "extended" along the surface being irradiated at a lower working frequency to the "flattened" in this direction and extended along the axis of the transmitter 2 at an upper working frequency. As a result, the whole volume of a tissue cooled by the cryodestructor 3 will be subjected to a uniform (averaged in time) influence of the ultrasound.

In the embodiment of the instrument, corresponding to FIG. 8, both the transmitters 2 and 15 are brought into contact with the tissue to be destructed.

By supplying the coolant medium through the conduits 8 into the cryodestructor 3, the tissue is cooled within a zone defined by a radius which is greater by 2 cm than the radius of the working portion 4 of the cryodestructor 3. The ultrasonic influence within the limits of the radius of the working portion 4 is carried out by the transmitter 15 (whose diameter is equal to that of said portion), and beyond said radius said influence is accomplished by the transmitter 2, thermally insulated from the transmitter 15 to eliminate cryodestruction of tissues from the transmitter 2.

Due to such a design of the instrument, the working portion 4 of the cryodestructor 3 can be of any predetermined size, the congruency of zones of effective cryogenic and ultrasonic influences being complete.

The operation of the instrument constructed as shown in FIG. 9, can be demonstrated in an example of cryo-ultrasonic destruction of pathologic structures of a neck of the uterus.

To supply a coolant medium from the source 9 and to switch on the generator 5, the working portion 4 of the cryodestructor 3 is moved beyond the limits of the end surface 6 of the transmitter 2 by a distance depending on the distance and location of a pathologic region, and the cryodestructor 3 is fixed by the collet 23. The working surface 4 of the cryodestructor 3 and the surface 6 of the transmitter 2 are brought into contact with a neck of the uterus 27, having introduced the working portion 4 of the cryodestructor 3 into a cervical canal 28. A required quality of thermal and acoustic contacts is ensured by silicone oil or other suitable liquid.

Next, cryodestruction of tissues is accomplished in a zone 29 of pathology by supplying the coolant medium from the source 9 into the working portion 4 of the cryodestructor 3. Under the effect of thermal resistance of tissues, the zone of cryodestruction takes the shape shown in FIG. 9 and corresponding to the zone 29 of pathology.

Simultaneously with cryodestruction, the neck of the uterus 27 is irradiated with ultrasound. The body of the uterus 27, solidified by freezing, is in the zone 29 of pathology a waveguide for ultrasonic oscillations, wherein the ultrasound is reflected repeatedly, thereby forming an ultrasonic field of a required intensity over the whole zone of cryodestruction.

The operation of the instrument illustrated in FIGS. 10, 11, and 12, does not differ in principle from the above described operation of the instrument shown in FIG. 1 except that the surface 6 of acoustic contact in the instruments corresponding to FIGS. 10 and 11 is a side surface of a solid of revolution, and in the instrument illustrated in FIG. 12, side and end surfaces, which fact stipulates application of these modifications for carrying out operations on tubular organs.

The instrument constructed as shown in FIG. 11 can be of a length which is smaller than that of the zone being destructed due to an increased width of the directional pattern of the ultrasonic beam, mentioned above.

The efficiency of cryo-ultrasonic influence on pathologic structures of tissues is further explained in terms of specific embodiments carried out on animals.

Four groups of white randomly bred rats were taken for the tests. In the first group, median laparotomy was carried out using the conventional procedure. A spleen was extracted from the abdominal cavity under sterile conditions, following which said spleen was again sunk into said cavity, and the operative wound was sutured.

In the second group laparotomy and extraction of the spleen were supplemented by irradiating said spleen, under sterile conditions, with a subliminal dose of ultrasonic oscillations in a pulse mode and during one minute, the power density being of 2 W/cm$^2$, with subsequent sinking the spleen into the abdominal cavity and suturing the operative wound.

Irradiation was accomplished by a commercial ultrasonic therapeutic instrument having oscillation frequency of 2640 kHz, pulse width of 10 ms, and pulse frequency of 50 Hz.

In the third group, after carrying out laparotomy, the spleen was partially frozen, under sterile conditions, for 1 minute, the temperature at the probe being of $-150°$ C., by means of a device for locally freezing biological tissues disclosed in USSR Inventor's Certificate No. 342,387 and having a probe diameter of 4 mm. Liquid nitrogen was utilized as a coolant medium. Following this, the spleen was sunk into the abdominal cavity and the operative wound was sutured.

In the fourth main experimental group the spleen, which has been extracted after laparotomy, was subjected during one minute to freezing at temperature $-150°$ C. within a selected region, and to irradiation in a pulse mode with a subliminal dose of ultrasonic oscillations having the power density of 2 W/cm$^2$, the cryo-ultrasonic instrument of the invention being utilized for this purpose.

Following the treatment, the spleen was sunk into the abdominal cavity and the operative wound was sutured.

After 3, 7 and 10 days following the experiment, equal quantities of animals from each group were killed, subjected to autopsy, and spleen preparations thus obtained were subjected to morphologic and histochemical studies.

The studies have demonstrated that irradiation with subliminal doses of ultrasound does not practically influence the structure of a tissue, and simple cooling results only in a partial lesion of cells and elements of connective tissue.

In the combined influence of deep freezing and ultrasound in subliminal doses, no normal cellular elements are present within the zone of necrosis.

The efficiency of cryo-ultrasonic influence on pathologic structures of tissues has been confirmed by the results of treating patients. In 1978–1979, 280 patients were treated by the cryoultrasonic instrument of the invention at the Department of head and neck tumors of the Oncologic Scientific Center of the USSR Academy of Medical Sciences and Obstetric-Gynecologic Clinics of the Odessa Medical Institute.

Liquid nitrogen at a temperature of $-196°$ C. was used as a coolant medium. Frequency of ultrasonic oscillation was 880 kHz, intensity, 0.2 W/cm$^2$, and the influence time was 1 to 5 minutes in the continuous mode.

As a result of the conducted clinical studies it has been found that combined utilization of ultrasound and low temperatures allows the amount of necrotized tissue to be increased, reparation terms to be shortened 2 to 3 times, treatment to be accelerated 1.5 to 2 times.

While particular embodiments of the invention have been shown and described, various modifications thereof will be apparent to those skilled in the art and therefore it is not intended that the invention be limited to the disclosed embodiments or to the details thereof and the departures may be made therefrom within the spirit and scope of the invention as defined in the claims.

What is claimed is:

1. A surgical instrument for simultaneously cooling and ultrasonically irradiating tissue, comprising:
    a housing having a generally annular ultrasonic transmitter secured thereto, for generating acoustic ultrasonic vibrations in response to electrical signals of ultrasonic frequency, said ultrasonic transmitter having an end surface portion for emitting acoustic ultrasonic radiation, and a cavity within said transmitter and adjacent said end surface portion thereof;
    a cryodestructor having a working portion disposed in said cavity;
    conduit means within said housing for providing communication between a coolant medium source and said working portion of said cryodestructor; and
    means for coupling said ultrasonic transmitter to a generator of electrical signals of ultrasonic frequency.

2. A surgical instrument as claimed in claim 1 wherein said ultrasonic transmitter is made as a solid of revolution with a side surface of revolution and an end surface comprising said end surface portion, and is provided with a central bore comprising said cavity.

3. A surgical instrument as claimed in claim 2, wherein the end surface portion of said ultrasonic transmitter is a surface of acoustic contact, said transmitter being provided with an inner surface which is opposite to the surface of acoustic contact, both said end surface portion and said inner surface being curvilinear, the thickness of said end surface portion of said transmitter between said end surface and said inner surface increasing from the central bore toward the periphery thereof.

4. A surgical instrument as claimed in claim 3, wherein the central bore of said transmitter is blind, at least a bottom portion of the wall of said bore serving simultaneously as said working portion of said cryodestructor.

5. A surgical instrument as claimed in claim 4, wherein the surface of acoustic contact of said ultrasonic transmitter is outwardly convex, said acoustic contact surface and the inner surface opposite thereto being spherically shaped and said surfaces having radii R and r respectively, determined from the following expressions:

$$R = D/(2 \sin \phi_o),$$

$$r = R[1 - \cos \phi_o + \sin \phi_o \cdot \text{ctg}(\phi_o + 90°)] - t_o,$$

$$\phi_o = 45° - \alpha - \arcsin 0.56 (V_o/V),$$

$$\alpha = \arcsin 0.52 (\lambda/D),$$

where

D is the diameter of the surface of acoustic contact of the ultrasonic transmitter, $t_o$ is the minimum thickness of the ultrasonic transmitter between the surface of acoustic contact and the inner surface opposite thereto, $\lambda$ is the ultrasonic wavelength within a medium being irradiated, $V_o$ is the speed of ultrasonic wave propagation in a medium being irradiated, and V is the speed of ultrasonic wave propagation within said ultrasonic transmitter.

6. A surgical instrument as claimed in claim 3, further comprising a generator of electrical signals of ultrasonic frequency coupled to said ultrasonic transmitter via said coupling means, comprising a master oscillator, a wave generator of sinusoidal oscillations, freguency modulation means for frequency modulating the output of said master oscillator in accordance with the output of said wave generator, and amplitude modulation means for amplitude modulating the output of said master oscillator in accordance with the output of said frequency modulation means.

7. A cryo-ultrasonic surgical instrument as claimed in claim 2, provided with an additional ultrasonic transmitter mounted adjacent said working portion of said cryodestructor, said additional ultrasonic transmitter being thermally insulated from said ultrasonic transmitter having said cryodestructor mounted within the cavity thereof, and means for coupling the additional ultrasonic transmitter to a generator of electrical signals of ultrasonic frequency.

8. A surgical instrument as claimed in claim 2, wherein said cryodestructor is axially movable within the central bore of said ultrasonic transmitter.

9. A surgical instrument as claimed in claim 2, wherein at least a portion of the side surface of revolution of said ultrasonic transmitter is a surface of acoustic contact, said transmitter being provided with an inner surface of revolution which is opposite to said surface of acoustic contact.

10. A cryo-ultrasonic surgical instrument as claimed in claim 9, wherein said transmitter has a central portion and end faces, and the generatrices of the surface of acoustic contact and the inner surface of revolution of said ultrasonic transmitter opposite to the surface of acoustic contact are curvilinear, the thickness of said transmitter between said surfaces increasing in the longitudinal direction from the central portion toward the end faces of said transmitter.

11. A cryo-ultrasonic surgical instrument as claimed in claim 10, wherein the surface of acoustic contact of said ultrasonic transmitter is outwardly convex and spherical, the inner surface of revolution opposite thereto also being spherical.

12. A cryo-ultrasonic surgical instrument as claimed in claim 11, further comprising a generator of electrical signals of ultrasonic frequency coupled to said ultrasonic transmitter via said coupling means and comprising a master oscillator and, in series connection, a generator of sinusoidal oscillations, a frequency modulator of ultrasonic oscillations and an amplitude modulator of ultrasonic oscillations, said modulators having control inputs connected to at least one output terminal of said master oscillator.

13. A surgical instrument as claimed in claim 2, wherein the side surface of said ultrasonic transmitter is smoothly coextensive with the end surface thereof, so that said side and end surfaces cooperate to form a common surface of acoustic contact.

* * * * *